United States Patent [19]

Gibson et al.

[11] Patent Number: 4,864,236
[45] Date of Patent: Sep. 5, 1989

[54] WIRE INHOMOGENEITY DETECTOR HAVING A CORE WITH OPPOSING POLE PIECES AND GUIDE PIECES ADJACENT THE OPPOSING POLE PIECES

[75] Inventors: George H. Gibson; Robert G. Smits, both of Lafayette; Philippe H. Eberhard, El Cerrito, all of Calif.

[73] Assignee: The United States of America as represented by the United States Department of Energy, Washington, D.C.

[21] Appl. No.: 413,589

[22] Filed: Aug. 31, 1982

[51] Int. Cl.[4] .................... G01N 27/72; G01N 27/82; G01R 33/12
[52] U.S. Cl. .................................. 324/238; 324/234; 324/236
[58] Field of Search ........ 324/234, 222, 223, 236–238, 324/DIG. 1; 331/65

[56] References Cited

U.S. PATENT DOCUMENTS

| | | | |
|---|---|---|---|
| 2,534,420 | 12/1950 | Delaney | 324/222 |
| 2,918,631 | 12/1959 | Callan et al. | 324/238 |
| 2,960,652 | 11/1960 | Harris et al. | 324/222 |
| 3,056,081 | 9/1962 | Hochschild | 324/238 |
| 3,281,678 | 10/1966 | Cilyo | 324/243 |
| 3,283,245 | 11/1966 | Stauffer | 324/64 |
| 4,303,885 | 12/1981 | Davis et al. | 324/237 |

FOREIGN PATENT DOCUMENTS

| | | | |
|---|---|---|---|
| 0024593 | 2/1977 | Japan | 324/234 |
| 0063756 | 5/1980 | Japan | 324/240 |

OTHER PUBLICATIONS

Gibson et al., "Detecting . . . With an Eddy Current Delector", Group A Physics Natl. #918, 8/1981, Univ. of Calif., Berkeley, Calif., pp. 1–11.

Primary Examiner—Reinhard J. Eisenzopf
Assistant Examiner—W. Snow
Attorney, Agent, or Firm—L. E. Carnahan; Roger S. Gaither; Judson R. Hightower

[57] ABSTRACT

A device for uncovering imperfections in electrical conducting wire, particularly superconducting wire, by detecting variations in eddy currents. Eddy currents effect the magnetic field in a gap of an inductor, contained in a modified commercial ferrite core, through which the wire being tested is passed. A small increase or decrease in the amount of conductive material, such as copper, in a fixed cross section of wire will unbalance a bridge used to measure the impedance of the inductor, tripping a detector and sounding an alarm.

11 Claims, 1 Drawing Sheet

WIRE INHOMOGENEITY DETECTOR HAVING A CORE WITH OPPOSING POLE PIECES AND GUIDE PIECES ADJACENT THE OPPOSING POLE PIECES

The invention described herein arose at the Lawrence Berkeley Laboratory in the course of, or under Contract No. DE-AC03-76SF00098 between the U.S. Department of Energy and the University of California.

BACKGROUND OF THE INVENTION

This invention relates to the testing of wire, particularly to the testing of the conductive properties of a wire, and more particularly to a detector assembly for testing wire inhomogeneity to determine possible defects in the wire.

Various applications establish a need for determining the electrical properties of wire prior to use of the wire. For example, superconducting magnets typically require thousands of meters of superconducting wire. All too frequently, the superconductor is flawed, and there has been no convenient method for determining where the defects, if any, occur.

The operation of building a coil from conductive wire, for example, is extremely time-consuming and expensive. Furthermore, construction techniques for many superconducting magnets prevent replacement of wire after the coil has been completed. For this reason, every effort must be made to find any defects in the wire before assembling the coil. Traditional testing methods examine small segments of wire from the ends of the roll, but do not inspect the overall conductor quality. Occlusions, losses of superconducting filaments, or changes in cross section of the wire may be undetected and, thus, prevent the magnet's proper performance.

Various types of apparatus and methods have been developed for testing various properties of wire. For example, U. S. Pat. Nos. 2,960,652 issued Nov. 15, 1960 to W. P. Harris et al and 3,281,678 issued Oct. 25, 1966 to F. F. Cilyo are directed to determining the magnetic properties of the wire. U.S. Pat. No. 4,303,885 issued Dec. 1, 1981 to T. J. Davis relates to a digitally controlled eddy current test apparatus for detecting a flaw location in a wire. U.S. Pat. No. 3,283,245 issued Nov. 1, 1966 to R. A. Stauffer provides a testing method for the superconductivity wherein the superconductor is dipped in a cryogenic bath.

While these prior methods and apparatus have been effective for their intended purpose, a need has existed for a simple, but effective method for detecting inhomogeneity in a conductive wire over its entire length, especially superconducting wire to be utilized in magnets, etc.

Also, while eddy currents have been previously used to measure the quality of a copper surface, e. g., in radio frequency cavities, there is a need for a device that measures variations in eddy currents to reveal defects in wire, particularly superconducting wire, by gauging the proportion of conductive material in the wire in a given cross section.

SUMMARY OF THE INVENTION

The present invention fills the above-mentioned needs by providing a device for detecting variations in the conductive properties along the length of a wire.

Therefore, an object of this invention is to provide a device capable of determining the material composition of a conductor along its entire length.

A further object of the invention is to provide a wire inhomogeneity detector assembly.

Another object of the invention to provide a device for uncovering imperfections in superconducting wire by detecting variations in eddy currents.

Another object of the invention is to provide a device for finding occlusions, losses of superconducting filaments, or changes in the cross section or the copper content of a copper-stabilized superconducting wire.

Other objects of the invention will become apparent to those skilled in the art from the following description and accompanying drawings.

Basically, the above-listed objects of this invention are carried out by a device composed of a coil assembly through which the wire being tested passes and to which is electrically connected an impedance bridge, to the output terminals of which are connected an oscilloscope and a filter-detector-alarm. The coil assembly includes a ferrite core having two opposing poles, the area of each of the poles is approximately equal to the squared width of the wire being tested, and a coil inside the core which generates a field that is passed through the wire via the ferrite poles. The impedance bridge, which is adjusted until a null balance point is achieved, measures the impedance of the inductor and reveals changes in eddy currents. The filter detector alarm includes an input bandpass filter (designed to pass the fundamental frequency of the bridge and to remove the harmonics) which is attached to a differential comparator with the threshold set above the residual noise, the comparator, in turn, triggers an audible alarm. The oscilloscope is also connected to the detector output of the bridge and the null is easily observed thereon. Since the bridge is set at the null balance point, any increase or decrease in eddy currents inside the coil assembly will cause a change in the bridge output. A small increase or decrease in the amount of copper, for example, in the wire being tested, alters the eddy current losses changing the balance of the bridge, thus sounding the alarm.

DETAILED DESCRIPTION OF THE INVENTION

The invention involves a wire inhomogeneity detector assembly for uncovering imperfections in electrical conductive wire by detecting variations in eddy currents caused by the variations of the wire size, composition, or conductive properties of the wire. While the invention is described hereinafter with respect to testing of a copper-stabilized superconducting wire, such as rectangular shaped Cu:NbTi wire, it is not intended to limit the invention to any specific type or compostion of wire, since the invention can be utilized for testing various types of conductive wires.

Figure 1:
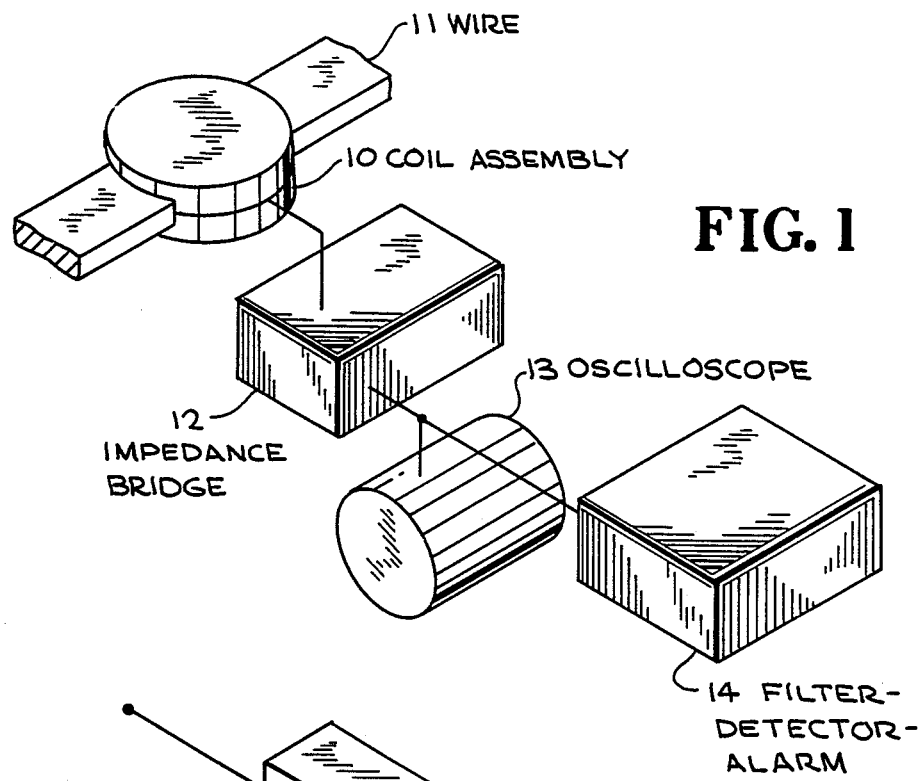
FIG. 1 illustrates an embodiment of the wire inhomogeneity detector made in accordance with the invention.

The wire inhomogeneity detector assembly of this invention, illustrated in the FIG. 1 embodiment, comprises a coil assembly 10 through which a wire 11 to be tested is passed, and to which is connected an impedance bridge 12, the output of bridge 12 being directed to an oscilloscope 13 and to a filter detector alarm assembly 14.

Figure 2:
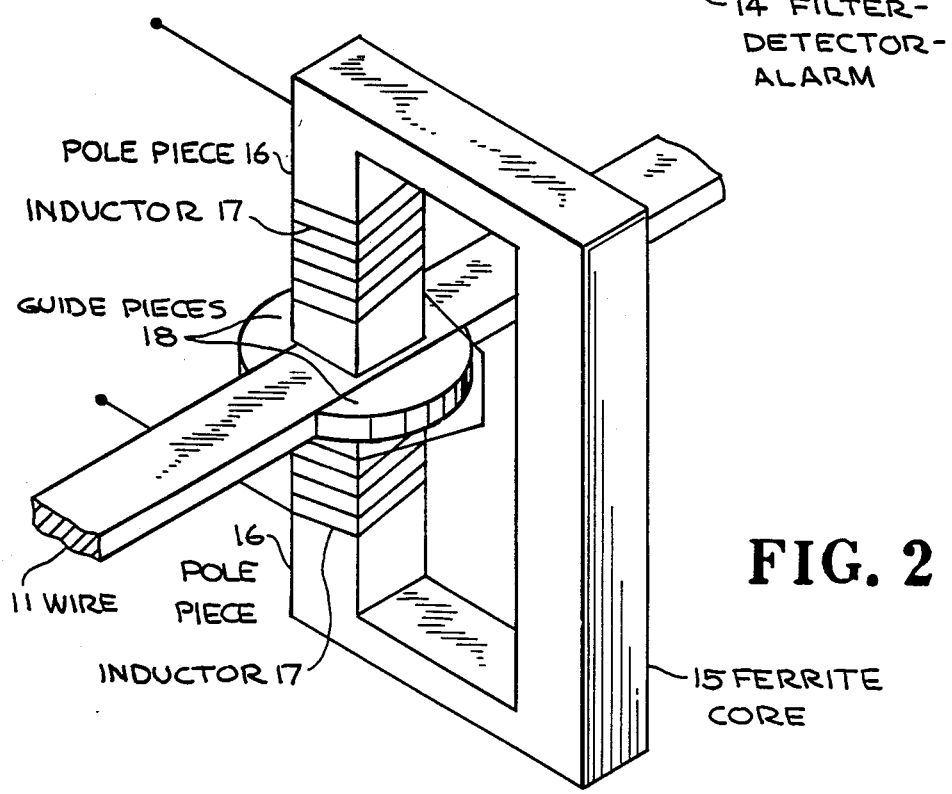
FIG. 2 schematically illustrates an embodiment of the coil assembly of the FIG. 1 detector.

The coil assembly 10, illustrated schematically in FIG. 2, basically consists of a ferrite core 15 having a pair of opposing pole pieces 16 on which are postioned series-aiding connected induction coils 17, and guide pieces 18, constructed of copper for example, through which the wire 11 passes.

In the embodiment illustrated in FIG. 1, and constructed to verify the invention, the coil assembly 10 of FIG. 2 was fabricated by modifying a standard ferrite pot core 15 such that most of the center material was removed except for the two opposing poles 16. The poles are of a square configuration with flat end surfaces, with the area of the poles being approximately equal to the squared width of the superconductor wire 11, i. e., about 3 mm for a 0.042×0.142 inch Cu:NbTi wire. The poles are spaced from each other a distance slightly greater than the thickness of the wire 11 passing therebetween. Machined copper block or guide pieces 18 are postioned in the space about poles 16 and guide the wire between the poles and function to reduce stray magnetic fields. A coil or inductor 17, wrapped around pole pieces 16, and connected to a power source (impedance bridge) not shown, generates a field that is passed through the superconducting wire 11 via the ferrite poles 16. The poles 16 may be of different cross-sectional configurations than that shown but need to have a width substantially equal to the width of the wire 11 passing therethrough.

The impedance bridge 12, such as a standard commercial bridge, type 1608-A made by General Radio Company, is connected to measure the impedance of the inductor 17, and reveals changes in eddy currents which effect the magnetic field in the gap of the inductor. The bridge 12 is adjusted until a null balance point is achieved. In the embodiment illustrated the bridge runs at 1,000 Hz and at null the residual signal is primarily the second harmonic, 2,000 Hz. By hooking up the bridge external output into the oscilloscope 13 (as well as to the filter detector alarm assembly 14) the null is easily observed.

The assembly 14 consists of a threshold detector and an audible alarm. The threshold detector consists of an input bandpass filter (designed to pass the fundamental frequency of the bridge and to remove the harmonics) attached to a differential comparator with the threshold set above the residual noise. The comparator, in turn, triggers the audible alarm. Other types of alarms, such as a flashing light, may be utilized if desired.

Since the bridge 12 is set at the null balance point, any increase or decrease in eddy currents inside the coil assembly 10 caused by an increase or decrease in the amount of copper in the wire 11 alters the eddy current losses changing the balance of the bridge 12, thus sounding the alarm of assembly 14. High sensitivity is achieved because there are two ferrite poles 16 between which the wire 11 passes, closely focusing the magnetic field through the wire. Also, there is only a small air gap.

The space left from missing superconducting filaments will increase the amount of copper in, or reduce the area of, the wire's cross section. A piece of slag or a possible occlusion of extra superconductor would reduce the amount of copper or increase the area of the wire's cross section. Any variations in the amount of copper in the wire are indicative of a probable flaw in the wire, and investigation of that section of wire should be performed.

The detector is also very sensitive to reduction in the width of the conductor or wire 11 because an air gap occurs between the conductor and copper guide-block 18 which passes considerable flux, looking like lost copper. Variation in wire width could indicate an accident in wire fabrication, and should, therefor be investigated.

If there is appreciable variation in the width of the conducting wire being tested, and thus a substantial unnecessary triggering of the alarm, the copper guide pieces 18 in coil assembly 10 can be spring loaded against the sides of the wire to avoid frequently setting off the alarm.

Also, if desired, sensitivity could be further enhanced by replacing the impedance bridge 12 with electronics specifically designed for use in this apparatus.

The wire inhomogeneity detector of this invention, described above, has been tested by eliminating and adding copper to some superconducting wire; results were positive for two types of tests. In a first test, notches of differing depths were mill cut across the 0.142 dimension of the superconducting wire having dimensions of about 0.042×0.142 inch. All notches were detectable. With the sensitivity necessary to detect a 0.062 inch wide×0.0019 inch deep notch, however, noise would too frequently trip the alarm. The sensitivity required to detect the 0.062 inch wide×0.004 inch deep notch tripped the alarm reliably. These results indicate that the existing system is sufficiently sensitive to detect a gain or loss of about 14% in copper content in this superconducting wire (Cu:NbTi), which is acceptable for magnet use. Some improvements in the electronics and coil assembly, as indicated above, could improve the system, if greater sensitivity were desired.

In the second test, two holes were drilled in the 0.042 inch sides of the superconducting wire and copper was soldered in place. This caused 25% of the NbTi to be replaced with copper. This test was equivalent to the change in the amount of copper to a 0.006 inch×0.062 inch notch of removed copper, each triggering the alarm at the same sensitivity setting on the detector. In this case, the wire inhomogeneity detector worked reliably and illustrated the ability of the detector to find changes below the surface of the wire.

Also, lengths of wire in excess of a thousand feet, made for use in the fabrication of superconducting magnets, have been continuously tested with excellent results, thus verifying the effectiveness of the invention.

It has thus been shown, that the present invention provides a device that measures variations in eddy currents to reveal defects in a conductive wire by gauging the proportion of conductive material in a given cross section of the wire. This is achieved by detecting a change in the impedance of an inductor. The change results from eddy currents caused by the magnetic flux channeled through pole pieces, aided by the copper wire guide, and through the wire to assess an increase or reduction of the conductive material in the wire. An additional advantage of this invention is that it determines the wire's interior electrical properties heretofore unattainable.

While a particular embodiment of the invention has been illustrated and described, modifications will become apparent to those skilled in the art, and it is intended to cover in the appended claims, all such modifications as come within the scope of the invention.

What is claimed is:

1. A wire inhomogeneity detector assembly for detecting changes in the conductive properties of a wire as the wire is passed therethrough comprising:
   a coil assembly through which a wire containing conductive material is adapted to be passed in a direction substantially perpendicular to a longitudinal axis of said coil assembly, said coil assembly comprising a single ferrite core having a pair of opposing pole pieces between which an associated conductive wire to be tested is adapted to be passed, each of said pole pieces having a coil wound therearound, said coil assembly including a guide-block consisting of a pair of guide pieces mounted adjacent to ends of said opposing pole pieces for guiding an associated conductive wire between said pole pieces and for reducing stray magnetic field lines, said guide pieces being positioned closely adjacent an associated conductive wire passing therebetween;
   an impedance bridge adjusted to a null balance point operatively connected to said coil assembly which measures the impedance of said coil assembly and is unbalanced by changes in eddy currents generated in said coil assembly; and
   a filter detector alarm assembly operatively connected to an output of said impedance bridge, said filter detector alarm assembly including an input bandpass filter operatively connected to a differential comparator, the output of which triggers an alarm.

2. The detector assembly of claim 1, wherein said coils are wound around each of said pole pieces in a series-aiding connection, said pole pieces having a width substantially equal to a width of a wire to be passed therethrough, whereby the coil generates a field that is adapted to be passed through an associated conductive wire via said pole pieces, such that changes in eddy currents created therein is detected by said bridge.

3. The detector assembly of claim 2, wherein said guide pieces are constructed of copper, and wherein the conductive wire is a copper stabilized superconducting wire.

4. The detector assembly of claim 3, wherein said copper stabilized superconducting wire is constructed of CuNbTi, and whereby variations in eddy currents are caused by an increase or decrease in the amount of copper in a fixed cross section of said wire.

5. The detector assembly of claim 1, wherein said opposing pole pieces each have an area approximately equal to the squared width of a conductive wire passed therebetween.

6. The detector assembly of claim 1, additionally including means for observing the output of said impedance bridge.

7. The detector assembly of claim 6, wherein said means constitutes an oscilloscope operatively connected to an output of said bridge.

8. The detector assembly of claim 1, wherein said alarm is of an audible type.

9. The detector assembly of claim 1, wherein said pair of opposing pole pieces are each of a substantially square configuration with a flat end surface.

10. The detector assembly of claim 9, wherein said end surfaces of said pair of pole pieces have an area about equal to the squared width of an associated conductive wire passed therebetween.

11. The detector assembly of claim 1, wherein said coils are wound on said opposing pole pieces in a series-aiding arrangement.

* * * * *